United States Patent [19]

Fischer

[11] Patent Number: 4,742,167
[45] Date of Patent: May 3, 1988

[54] BIOLOGICALLY ACTIVE N-PYRAZINYL-HALOACETAMIDES

[75] Inventor: Gordon C. Fischer, Angleton, Tex.

[73] Assignee: The Dow Chemical Company, Midland, Mich.

[21] Appl. No.: 868,965

[22] Filed: May 30, 1986

[51] Int. Cl.[4] .................. C07D 241/16; C07D 241/18; A01N 43/60

[52] U.S. Cl. .................................... 544/336; 544/408; 544/409

[58] Field of Search .................. 544/336, 408, 409

[56] References Cited

U.S. PATENT DOCUMENTS

| | | | |
|---|---|---|---|
| 3,007,786 | 11/1961 | Hamm et al. | 71/2.3 |
| 3,356,724 | 12/1967 | Olin | 260/561 |
| 3,574,746 | 4/1971 | Chupp et al. | 260/561 |
| 3,608,087 | 9/1971 | Patchett et al. | 424/320 |
| 4,359,576 | 11/1982 | Ten Haken et al. | 544/336 |
| 4,414,215 | 11/1983 | Hartman | 424/250 |
| 4,441,912 | 4/1984 | Ten Haken et al. | 71/92 |
| 4,460,403 | 7/1984 | Takematsu et al. | 71/93 |

OTHER PUBLICATIONS

CA 54:12310, Nagasawa, M. et al., (1961).
CA 52:9507g, Nagasawa, M. et al., (1959).
CA 79:1347m, Gimesi, A. et al., (1973).

*Primary Examiner*—Donald G. Daus
*Assistant Examiner*—William A. Teoli, Jr.
*Attorney, Agent, or Firm*—Daniel N. Lundeen; A. Cooper Ancona

[57] ABSTRACT

N-Pyrazinyl-haloacetamide having insecticidal, herbicidal, or fungicidal activity. The compound has the general formula:

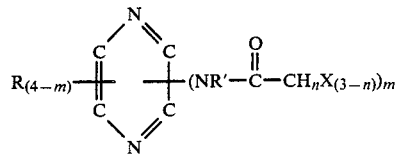

wherein R is hydrogen, hydrocarbyl, halogen, epoxy, hydroxy, alkoxy, mercapto, alkylthio, nitro, cyano or amino; R' is hydrogen or hydrocarbyl; X is halogen; m is an integer from 1 to 4; and n is 0, 1 or 2. The compound may also be a tautomer or acid addition salt of this formula.

17 Claims, No Drawings

BIOLOGICALLY ACTIVE N-PYRAZINYL-HALOACETAMIDES

FIELD OF THE INVENTION

The present invention is directed to N-pyrazinyl-haloacetamides which have biological activity as herbicides, insecticides, microbiocides or plant growth regulators.

DESCRIPTION OF THE INVENTION

The novel compounds of the present invention are N-pyrazinyl-haloacetamides of the formula:

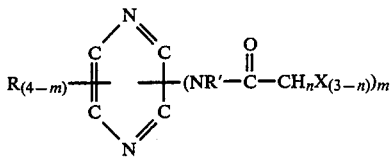

wherein each R is a radical independently selected from: hydrogen; hydrocarbyl radicals having from 1 to about 10 carbon atoms, preferably from 1 to about 6 carbon atoms; halide; epoxy; —OR" in which R" is hydrogen or a hydrocarbyl radical having from 1 to about 10 carbon atoms, preferably from 1 to about 6 carbon atoms; —SR" in which R" is hydrogen or a hydrocarbyl radical having from 1 to about 10 carbon atoms, preferably from 1 to about 6 carbon atoms; nitro; cyano; and —NR"$_2$ in which each R" is independently hydrogen or a hydrocarbyl radical having from 1 to about 10 carbon atoms, preferably from 1 to about 6 carbon atoms;

each R' is independently hydrogen or hydrocarbyl radical having from 1 to about 10 carbon atoms, preferably from 1 to about 6 carbon atoms;

X is halogen selected from chlorine, bromine, fluorine and iodine, preferably chlorine;

n is an integer from 0 to 2; and m is an integer from 1 to 4. The compounds of the invention also include the biologically active acid addition salts and tautomers corresponding to the foregoing formula.

Particularly preferred as having insecticidal activity for the family Tetranychidae (spider mites) are the N-pyrazinyl-haloacetamides of the above formula in which n is 2, e.g. 2-chloro-N-(2-pyrazinyl)-acetamide.

Particularly preferred as having herbicidal and plant growth regulating activity for broadleaf grasses, grassy weeds, and broadleaf crops are the N-pyrazinyl-haloacetamides of the above formula in which n is zero, e.g. 2,2,2-trichloro-N-(2-pyrazinyl)-acetamide.

The present N-pyrazinyl-haloacetamides are generally prepared by reacting 2-haloacetyl halide with the appropriate aminopyrazine in an inert organic solvent in the presence of an acid scavenger. Suitable inert solvents include, for example, ethyl acetate, ethyl ether, petroleum ether, tetrahydrofuran, acetonitrile, toluene, and the like. Typical acid scavengers include, for example, triethylamine, sodium carbonate, sodium bicarbonate, calcium carbonate, calcium bicarbonate, dimethyl benzylamine, sodium acetate, and the like. Generally, the reaction is carried out at room temperature and is completed in ½-4 hours with stirring. The product is generally recovered by evaporating the solvent following the reaction.

In using the present N-pyrazinyl-haloacetamides, it may be applied to the area to be treated in the form of wettable powder, dust, granules, solution, emulsion, suspension or aerosol as desired at an effective rate.

EXAMPLE 1

Into a 250 ml round-bottom flask equipped with a magnetic stirrer were placed 7.00 g (0.07 mol) aminopyrazine, 150 ml anhydrous ethyl acetate and 7.49 g (0.07 mol) triethylamine as an HCl scavenger. After complete dissolution of the aminopyrazine, an argon atmosphere was maintained and 8.36 g (0.07 mol) 2-chloroacetyl chloride was added with a syringe pump over a one-hour period while stirring. The reaction temperature was about 23°–25° C. After stirring for an additional one-half hour, the ethyl acetate was removed by vacuum distillation at room temperature to precipitate the reaction product. The product was dissolved and ultrasonicated in about 400 ml methylene chloride, washed with deionized water, dried over magnesium sulfate, and filtered. The methylene chloride was then removed by vacuum distillation at room temperature.

The product was a light green solid, m.p. 143°–145° C. The chemical structure for N-(2-pyrazinyl)-2-chloroacetamide was verified by NMR, IR and GC analytical methods.

The product was screened for insecticidal and herbicidal activity, and was found to have insecticidal activity for two-spotted spider mites. At 800 ppm, about 95 percent of the mites were killed. The results are presented in Table I.

TABLE I

Biological Activity Screening of 2-Chloro-N—pyrazinyl Acetamide

| Species | Test Method | Concentration | Percent Inhibition |
|---|---|---|---|
| Tobacco Budworm | A[1] | 800 ppm | 0 |
| Beet Army worm larvae | A | 800 ppm | 0 |
| Western spotted cucumber beetle larvae | B[2] | 75 ppm | 0 |
| Two-spotted spider mite | C[3] | 800 ppm | 95 |
| Nutsedge | D[4] | 4000 ppm | 0 |
| Pig weeds | D | 4000 ppm | 0 |
| Pig weeds | E[5] | 1.12 g/m$^2$ | 0 |
| Cotton | D | 4000 ppm | 0 |
| Cotton | E | 1.12 g/m$^2$ | 0 |
| Crabgrass | D | 4000 ppm | 0 |
| Crabgrass | E | 1.12 g/m$^2$ | 0 |
| Water grass | D | 4000 ppm | 0 |
| Water grass | E | 1.12 g/m$^2$ | 0 |
| Wild oats | D | 4000 ppm | 0 |
| Wild oats | E | 1.12 g/m$^2$ | 0 |
| Yellow Foxtail | D | 4000 ppm | 0 |
| Yellow Foxtail | E | 1.12 g/m$^2$ | 0 |
| Velvet leaf | D | 4000 ppm | 0 |
| Velvet leaf | E | 1.12 g/m$^2$ | 0 |

Notes for Table I:

[1]Test Method A: Three-inch discs of the indicated leaf (tobacco or beet) were treated in the diluted test material at the indicated concentration by spray or dip and placed in an open petry dish until dry. Test insects were put onto the treated leaf and the petry dish covered. Single mortality counts were made and recorded 2-5 days after keeping the covered petry dish in a moist atmosphere.

[2]Test Method B: Thirty grams of air-dried Davis soil were placed in a jar and treated with sufficient 800 ppm test chemical solution or dispersion to obtain the indicated concentration. The treated soil was dried for 24 hours and stirred well. In a plastic cup was placed 5 ml water, two corn seeds, 50-75 eggs, and the 30 g soil. The cup was capped with a plastic lid having a 3 mm hole in the center and stored at 27° F. and 60% relative humidity. The test was read 9-12 days later, noting live and dead larvae and any unhatched eggs.

[3]Test Method C: Test plants were grown singly in three-inch pots

TABLE I-continued and used before the primary leaves were fully expanded and before terminal growth occurred. Fifty to 100 mites or aphids as indicated were placed on the host plant and the plant was then dipped in the test chemical solution at the indicated concentration. Also, an additional application of the test chemical was made to the soil by an injection of the test chemical solution at approximately 2.2 g/m² with a syringe. The tests were conducted under greenhouse conditions (18-36° C.) and mortality checks made 3-6 days following treatment. Percent control was recorded after making any corrections for natural mortality in untreated checks.
[4]Test Method D: The indicated species were grown in plant bands to an average height of about 4 inches and sprayed to runoff with an aqueous solution or dispersion of the test chemical at the indicated concentrations. The plants were then held in greenhouse conditions for about 2 weeks before reading. Percent inhibition was determined by comparison to untreated plants, 0 indicating no visible effect and 100 indicating all plants dead.
[5]Test Method E: Seeds were planted in agricultural soil. Just after planting the diluted test chemical was sprayed on the soil at the indicated rate to drench the soil and allow the chemical to leach into the soil. The pots were maintained in variable greenhouse conditions (18-36° C.) and watered as necessary. Readings were taken about two weeks after treatment and percent inhibition determined as in Test Method E.

EXAMPLE 2

The procedure of Example 1 was repeated except that 10.90 g (0.07 mol) of 2,2-dichloroacetyl chloride was used instead of the 2-chloroacetyl chloride. The product N-(2-pyrazinyl)-2,2-dichloroacetamide was obtained as a brown semi-solid containing some unreacted aminopyrazine complexed therewith. The chemical structure was verified by NMR, IR and GC analytical techniques.

EXAMPLE 3

The procedure of Examples 1 and 2 was repeated except that 13.45 g (0.07 mol) of 2,2,2-trichloroacetyl chloride was used as the haloacetyl chloride. The product N-(2-pyrazinyl)-2,2,2-trichloroacetamide was obtained as a light tan solid, m.p. about 68° C., which also contained some unreacted aminopyrazine. The chemical structure was verified by NMR, IR and GC analytical methods.

The trichloro product was screened for biological activity as in Example 1, and was found to have pre-emergence herbicidal activity for various species. The results are presented in Table II.

TABLE II

Biological Activity Screening of 2,2,2-Trichloro-N—pyrazinyl Acetamide

| Species | Test Method | Concentration | Percent Inhibition |
|---|---|---|---|
| Tobacco budworm | A[1] | 800 ppm | 0 |
| Beet army worm larvae | A | 800 ppm | 0 |
| West spotted cucumber beetle larvae | B[2] | 75 ppm | 0 |
| Two-spotted spider mite | C[3] | 800 ppm | 0 |
| Nutsedge | D[4] | 4000 ppm | 0 |
| Nutsedge | E[5] | 0.11 g/m² | 0 |
| Nutsedge | E | 1.22 g/m² | 70 |
| Pig weeds | D | 4000 ppm | 0 |
| Pig weeds | E | 1.12 g/m² | 0 |
| Cotton | D | 4000 ppm | 0 |
| Cotton | E | 0.11 g/m² | 0 |
| Cotton | E | 0.22 g/m² | 30 |
| Cotton | E | 1.12 g/m² | 0 |
| Crabgrass | D | 4000 ppm | 0 |
| Crabgrass | E | 1.12 g/m² | 0 |
| Water grass | D | 4000 ppm | 0 |
| Water grass | E | 0.22 g/m² | 0 |
| Water grass | E | 1.22 g/m² | 100 |
| Wild oats | D | 4000 ppm | 0 |
| Wild oats | E | 1.12 g/m² | 100 |
| Yellow foxtail | D | 4000 ppm | 0 |
| Yellow foxtail | E | 0.22 g/m² | 0 |
| Yellow foxtail | E | 1.22 g/m² | 100 |
| Velvet leaf | D | 4000 ppm | 0 |
| Velvet leaf | E | 0.22 g/m² | 0 |
| Velvet leaf | E | 1.12 g/m² | 0 |
| Morning glory | D | 4000 ppm | 0 |
| Morning glory | E | 0.22 g/m² | 0 |
| Morning glory | E | 1.22 g/m² | 0 |
| Soybean | E | 0.22 g/m² | 0 |
| White winter wheat | E | 0.03 g/m² | 0 |
| White winter wheat | E | 0.06 g/m² | 50 |
| White winter wheat | E | 0.11 g/m² | 50 |
| White winter wheat | E | 0.22 g/m² | 50 |
| Corn | E | 0.11 g/m² | 0 |
| Corn | E | 0.22 g/m² | 50 |
| Sorghum/milo | E | 0.11 g/m² | 0 |
| Sorghum/milo | E | 0.22 g/m² | 30 |
| Johnson grass | E | 0.22 g/m² | 0 |
| Sugar beets | E | 0.22 g/m² | 0 |
| Rape | E | 0.11 g/m² | 0 |
| Rape | E | 0.22 g/m² | 40 |
| Cultured rice | E | 0.11 g/m² | 0 |
| Cultured rice | E | 0.22 g/m² | 100 |
| Jimson weed | E | 0.22 g/m² | 0 |
| Species 19184 | E | 0.11 g/m² | 0 |
| Species 19184 | E | 0.22 g/m² | 20 |

Notes for Table II:
[1]See Table I, note 1.
[2]See Table I, note 2.
[3]See Table I, note 3.
[4]See Table I, note 4.
[5]See Table I, note 5.

Having described my invention above, many variations in the illustrated details and specific materials, apparatus and procedures will occur to those skilled in the art. It is intended that all such variations which fall within the scope and spirit of the claims which follow be embraced thereby.

I claim:

1. An herbicidally or insecticidally active N-pyrazinyl-haloacetamide or a biologically active acid addition salt or tautomer thereof, said haloacetamide having the formula:

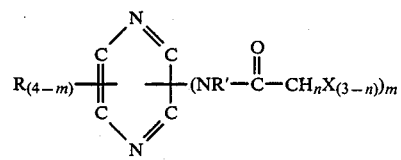

wherein each R is independently selected from the group consisting of:
hydrogen;
hydrocarbyl having from 1 to 10 carbon atoms;
halogen;
epoxy;
—OR″ in which R″ is hydrogen or hydrocarbyl having from 1 to 10 carbon atoms;
—SR″ in which R″ is hydrogen or hydrocarbyl having from 1 to 10 carbon atoms;
nitro;
cyano; and
NR₂″ in which each R″ is independently hydrogen or hydrocarbyl having from 1 to 10 carbon atoms;

wherein not more than one R is iodo or nitro and when m is less than 4 at least one R is halogen, epoxy, —OR", —SR", nitro, cyano, or NR$_2$";

wherein each R' is independently hydrogen or hydrocarbyl having from 1 to 10 carbon atoms;

wherein each X is halogen selected from the group consisting of chlorine, bromine, fluorine and iodine;

wherein n is 0, 1 or 2 and m is 1, 2, 3 or 4.

2. The haloacetamide of claim 1, wherein n is 2.

3. The haloacetamide of claim 1, wherein n is 0.

4. The haloacetamide of claim 1, wherein R" is hydrogen or hydrocarbyl having from 1 to 6 carbon atoms.

5. The haloacetamide of claim 1, wherein R' is independently hydrogen or hydrocarbyl having from 1 to 6 carbon atoms.

6. The haloacetamide of claim 1, wherein X is chlorine.

7. The haloacetamide of claim 1, wherein m is 1.

8. An insecticidally active 2-halo-N-(2-pyrazinyl)-acetamide or an insecticidally active acid addition salt or tautomer thereof, said acetamide having the formula:

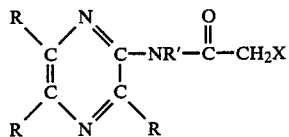

wherein each R is independently selected from the group consisting of:
hydrogen;
hydrocarbyl having from 1 to 10 carbon atoms;
halogen;
—OR" in which R" is hydrogen or hydrocarbyl having from 1 to 10 carbon atoms;
—SR" in which R" is hydrogen or hydrocarbyl having from 1 to 10 carbon atoms;
nitro;
cyano; and
NR"$_2$ in which each R" is independently hydrogen or hydrocarbyl having from 1 to 10 carbon atoms;
wherein not more than one R is iodo or nitro and at least one R is halogen, epoxy, —OR", —SR", nitro, cyano, or NR$_2$';
wherein R' is hydrogen or hydrocarbyl having from 1 to 10 carbon atoms; and
wherein X is halogen selected from chlorine, bromine, fluorine and iodine.

9. The haloacetamide of claim 8, wherein R' is hydrogen or hydrocarbyl having from 1 to 6 carbon atoms.

10. The haloacetamide of claim 8, wherein R" is hydrogen or hydrocarbyl having from 1 to 6 carbon atoms.

11. The haloacetamide of claim 8, where X is chlorine.

12. The haloacetamide of claim 10, wherein each R' is hydrogen.

13. An herbicidally active 2,2,2-trihalo-N-(2-pyrazinyl)-acetamide or a herbicidally active acid addition salt or tautomer thereof, said acetamide having the formula:

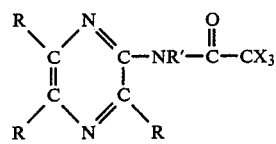

wherein each R is independently selected from the group consisting of:
hydrogen;
hydrocarbyl having from 1 to 10 carbon atoms;
halogen;
—OR" in which R" is hydrogen or hydrocarbyl having from 1 to 10 carbon atoms;
—SR" in which R" is hydrogen or hydrocarbyl having from 1 to 10 carbon atoms;
nitro;
cyano; and
NR"$_2$ in which each R" is independently hydrogen or hydrocarbyl having from 1 to 10 carbon atoms;
wherein not more than one R is iodo or nitro and at least one R is halogen, epoxy, —OR", —SR", nitro, cyano, or NR$_2$";
wherein R' is hydrogen or hydrocarbyl having from 1 to 10 carbon atoms; and
wherein X is halogen independently selected from chlorine, bromine, fluorine and iodine.

14. The haloacetamide of claim 13, wherein R' is hydrogen or hydrocarbyl having from 1 to 6 carbon atoms.

15. The haloacetamide of claim 13, wherein R" is hydrogen or hydrocarbyl having from 1 to 6 carbon atoms.

16. The haloacetamide of claim 13, wherein X is chlorine.

17. The haloacetamide of claim 16, wherein each R' is hydrogen.

* * * * *